(12) United States Patent
Ullrich et al.

(10) Patent No.: US 6,806,481 B2
(45) Date of Patent: Oct. 19, 2004

(54) RECTANGULAR FRAME SYSTEM WITH ONE TO TWO WINDOWPANE-LIKE RADIATION FILTERS AND A TANNING MODULE

(75) Inventors: Bernd Ullrich, Erlensee (DE); Ullrich Berger, Biebergemünd (DE); Ernst Smolka, Goldbach (DE); Jörn Jahnke, Hanau (DE); Stefan Greif, Fulda (DE)

(73) Assignee: Heraeus Noblelight GmbH, Hanau (DE)

( * ) Notice: Subject to any disclaimer, the term of this patent is extended or adjusted under 35 U.S.C. 154(b) by 420 days.

(21) Appl. No.: 09/988,806

(22) Filed: Nov. 20, 2001

(65) Prior Publication Data

US 2003/0075692 A1 Apr. 24, 2003

(30) Foreign Application Priority Data

Oct. 24, 2001 (DE) .................................... 201 17 228 U

(51) Int. Cl.[7] .............................................. G21G 5/00
(52) U.S. Cl. ...................... 250/504 R; 607/88; 607/90; 607/91
(58) Field of Search ................... 250/504 R; 607/88, 607/90, 91

(56) References Cited

U.S. PATENT DOCUMENTS

| | | | | |
|---|---|---|---|---|
| 4,194,125 A | * | 3/1980 | Wolff | ...................... 250/504 R |
| 4,560,883 A | * | 12/1985 | Kerschgens | .............. 250/504 R |
| 4,623,796 A | * | 11/1986 | Kratz | ...................... 250/504 R |
| 4,839,513 A | | 6/1989 | Wijtsma | |

FOREIGN PATENT DOCUMENTS

| | | |
|---|---|---|
| DE | 36 31 427 | 4/1976 |
| DE | 29 41 467 | 4/1981 |
| DE | 39 27 695 | 2/1991 |
| DE | 40 37 483 | 5/1992 |
| DE | 195 16 603 | 11/1996 |
| EP | 0 027 187 | 4/1981 |
| WO | 96/36390 | 11/1996 |

* cited by examiner

*Primary Examiner*—John R. Lee
*Assistant Examiner*—Paul M. Gurzo
(74) *Attorney, Agent, or Firm*—Fulbright & Jaworski L.L.P.

(57) ABSTRACT

The invention relates to a rectangular frame system with one to two discoid radiation filters, as well as a tanning module with such a frame system. The rectangular frame system has an upper plate, a lower plate and two to three margin members, two margin members being opposite one another and joining the upper plate to the lower plate, the upper plate having a first opening whose perimeter describes a circle, an ellipse, a rectangle or a polygon, and the lower plate has a rectangular second opening, the second opening having a greater area than the first opening, and at least two double spring clips are arranged at the two opposite margin members, which border on side of the frame system at which no margin member is provided, such that between the lower plate and the double spring clips a first radiation filter is clamped.

37 Claims, 8 Drawing Sheets

RECTANGULAR FRAME SYSTEM WITH ONE TO TWO WINDOWPANE-LIKE RADIATION FILTERS AND A TANNING MODULE

The invention relates to a rectangular frame system with one to two discoid radiation filters for filtering the spectrum of a tanning radiator as well as a tanning module with such a frame system.

The use of discoid radiation filters in tanning apparatus is known. For example, DE 29 41 467 A1 discloses a tanning module with a rectangular housing including a heat filter in a housing wall. A reflector is disposed in the housing, in which an ultraviolet filter is situated between the tanning radiator and the heat filter.

DE 195 16 603 A1 discloses a low-pressure viewing field for tanning apparatus, wherein a rectangular housing is used including reflector and filter pane. The housing is suitable for the installation of several UVC tubes. The side of the filter pane which faces the tubes is covered with a coating of UV phosphor pigments.

DE 36 31 427 C2 describes a radiation apparatus with a rectangular housing a reflector and a filter pane. To secure the filter pane against breaking a push switch is provided, which is held in its depressed position by the filter pane, but if the filter pane breaks it comes out of this position and shuts off the radiation source. The filter pane is fastened in the housing partially with a layer of adhesive.

DE 39 27 695 C2 discloses a tanning apparatus with a swivelling interference filter. In the direction of the emission of the radiation an infrared filter is placed. Depending on the inclination of the interference filter in the radiation emitting area the limit of the transmission spectrum is shifted to the short-wavelength UV B content or toward the long-wavelength UV A content. Thus the radiation spectrum can be adjusted to the skin type of the person being irradiated by swivelling of the filter.

DE 40 37 483 C2 describes an ultraviolet radiation apparatus with safety against breakage of a filter glass pane, wherein an electrical conductor carrying current is disposed on its perimeter. If the filter glass breaks the conductor is broken and the current is thus interrupted and the tanning radiator is turned off.

The problem presents itself of making available a rectangular frame system with one to two discoid radiation filters, which permits simple installation and removal and exchange of the radiation filter. The frame system is to be usable in a tanning module in a simple manner.

The problem is solved by a rectangular frame system having an upper plate, a lower plate and two to three marginal members, two marginal members lying opposite one another and joining the upper plate to the lower plate, the upper plate having a first opening whose perimeter describes a circle, an ellipse, a rectangle or a polygon, and the lower plate has a rectangular second opening, the second opening having a greater area than the first opening, and on the two opposite marginal members, which border on the side of the frame system on which no marginal member is provided, at least two double spring clips are arranged such that between the lower plate and the double spring clips a first radiation filter is clamped. Such a system permits a quick installation of the radiation filter without tools, because the radiation filters are clamped only by the double spring clips, and are not cemented or screwed. The frame system can be integrated easily into a tanning module.

It is preferred that the first radiation filter is an interference filter. The locking up of the first radiation filter is especially easy if it is of rectangular shape.

A width and one length of the first radiation filter ranging from 215 to 240 mm has proven desirable. It is preferred that the first radiation filter have a width of 225 mm and a length of 230 mm.

Between the upper plate and the two double spring clips a second radiation filter is preferably clamped and is ideally an ultraviolet filter or an infrared filter. The second radiation filter is preferably also of rectangular configuration.

The second radiation filter has proven practical in a width and length ranging from 215 mm to 240 mm. Preferably the second radiation filter has a width of 225 mm and a length of 230 mm.

The double spring clips are preferably half-way between the upper and the lower plate. Making the double spring clips from at least one bent metal wire is especially economical, the shape of the double spring clips represented in FIG. 3 or rather 3a being preferred. It is also possible to make a double spring clip from at least one piece of flat spring steel.

The double spring clips are ideally configured such that the first radiation filter can be inserted between the lower plate and the double spring clips from the side of the frame system on which no marginal member is present.

For the fastening of a second radiation filter the double spring clips are preferably configured such that the second radiation filter can be inserted from the side of the frame system on which no marginal member is present, between the upper plate and the double spring clips.

It has been found desirable to provide a non-slip back device for the one to two radiation filters on the side of the frame system on which no marginal member is present.

Furthermore, it has been found desirable to provide on the side of the frame system on which no marginal member is present a device to prevent the one to two radiation filters and/or a third marginal member from slipping through it.

Ideally, the first radiation filter has an imprint or an adhesive label on its side facing away from the second radiation filter. This imprint or adhesive label has preferably an opaque marginal area which optically conceals the marginal members.

The problem is furthermore solved by a tanning module with a housing, a tridimensional reflector disposed in or on the housing, as well as a rectangular frame system described above, on one side of the housing; the first radiation filter covers the radiation emitting area and the lower plate faces away from the reflector.

It is especially preferred that the rectangular frame system be releasable from the housing by means of a swinging mechanism and be thus replaceable. The swinging mechanism is to permit the radiation filter to be tilted with respect to the housing, and the release of the radiation filter from the housing is to be possible only after a displacement of the tilted radiation filter in the housing. Thus a user-friendly exchange of the radiation filter becomes possible and even an abrupt dropping of the radiation filter is prevented, since the radiation filter and its breakage are effectively prevented by such a swinging mechanism.

The rectangular frame system is ideally hooked into the housing; particularly an opening according to FIG. 7 in the housing is appropriate for hooking the frame system according to the invention in this manner.

The rectangular frame system is preferably fixed in position by means of a snap mechanism.

The perimeter of the reflector parallel to the radiation emitting area preferably describes a circle, an ellipse, a rectangle or a polygon. It is especially preferred if the reflector is formed of facets and the perimeter of the reflector parallel to the radiation emitting area describes a polygon of twelve corners.

It has been found desirable for the reflector to have a height of 90 mm to 95 mm, especially of 93.6 mm, and the dodecagon to have in the plane of the radiation emitting area a maximum diameter (corner to corner) in the range of 210 mm ro 230 mm, especially of 210 mm.

It has furthermore proven desirable if the reflector has a height ranging from 110 mm to 125 mm, especially 118.7 mm, and the dodecagon has a maximum diameter (corner to corner) ranging from 170 mm to 200 mm, especially 184 mm, in the plane of the radiation emitting area.

Furthermore, a reflector has proven desirable which has a height ranging from 75 mm to 90 mm, especially of 83.3 mm, and in which the dodecagon has a maximum diameter (corner to corner) in the plane of the radiation emitting surface ranging from 205 mm to 235 mm, especially 220 mm.

The FIGS. 1 to 8 are intended to explain the tanning module according to the invention by means of an example.

FIG. 2a shows the lower plate from FIG. 2 in a top plan view,

FIG. 3a shows double spring clip of FIG. 3 in a tridimensional view,

Figure 3:
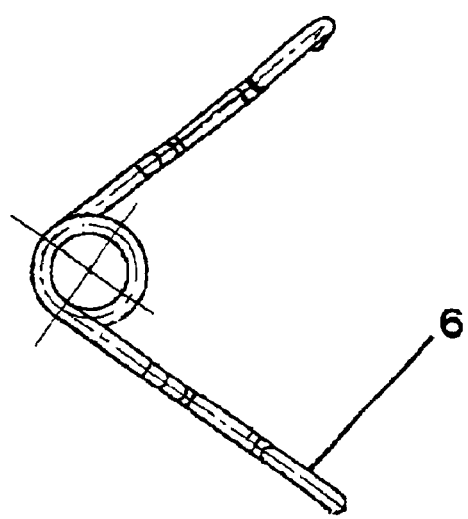
FIG. 3 shows a double spring clip.
Figure 3:
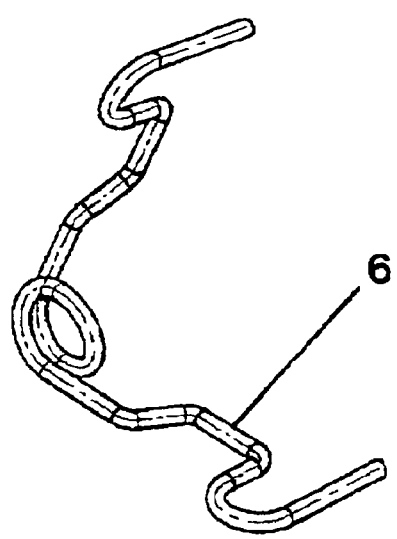
Figure 4:
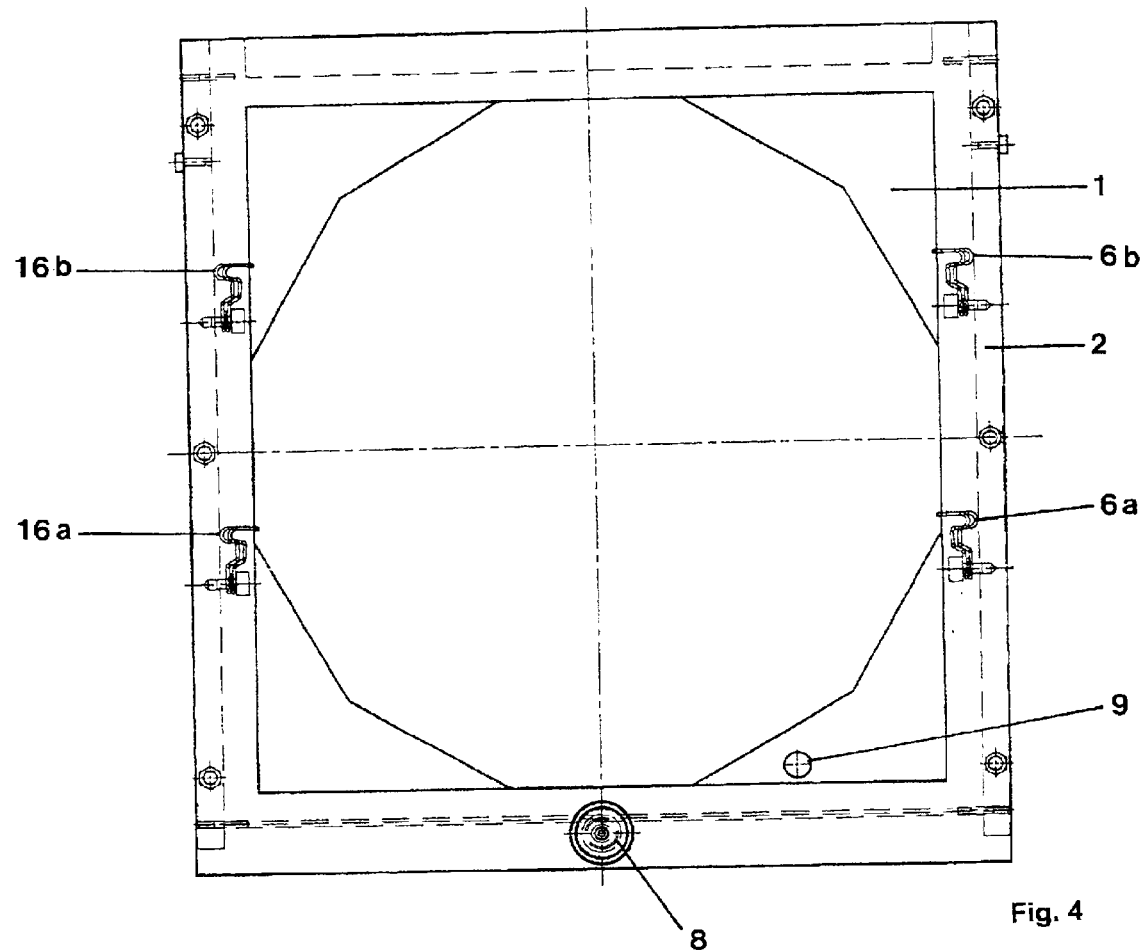
Figure 4:
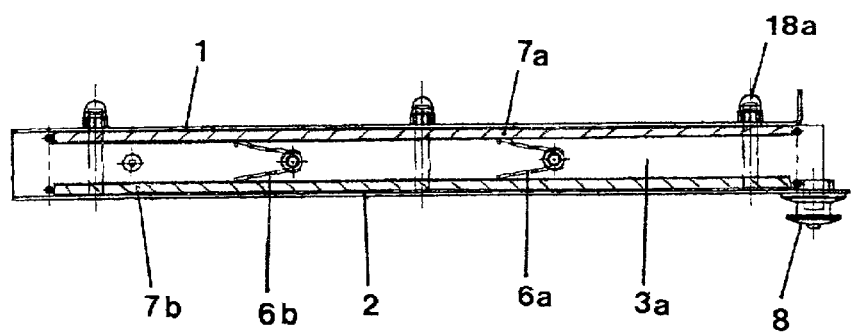
Figure 5:
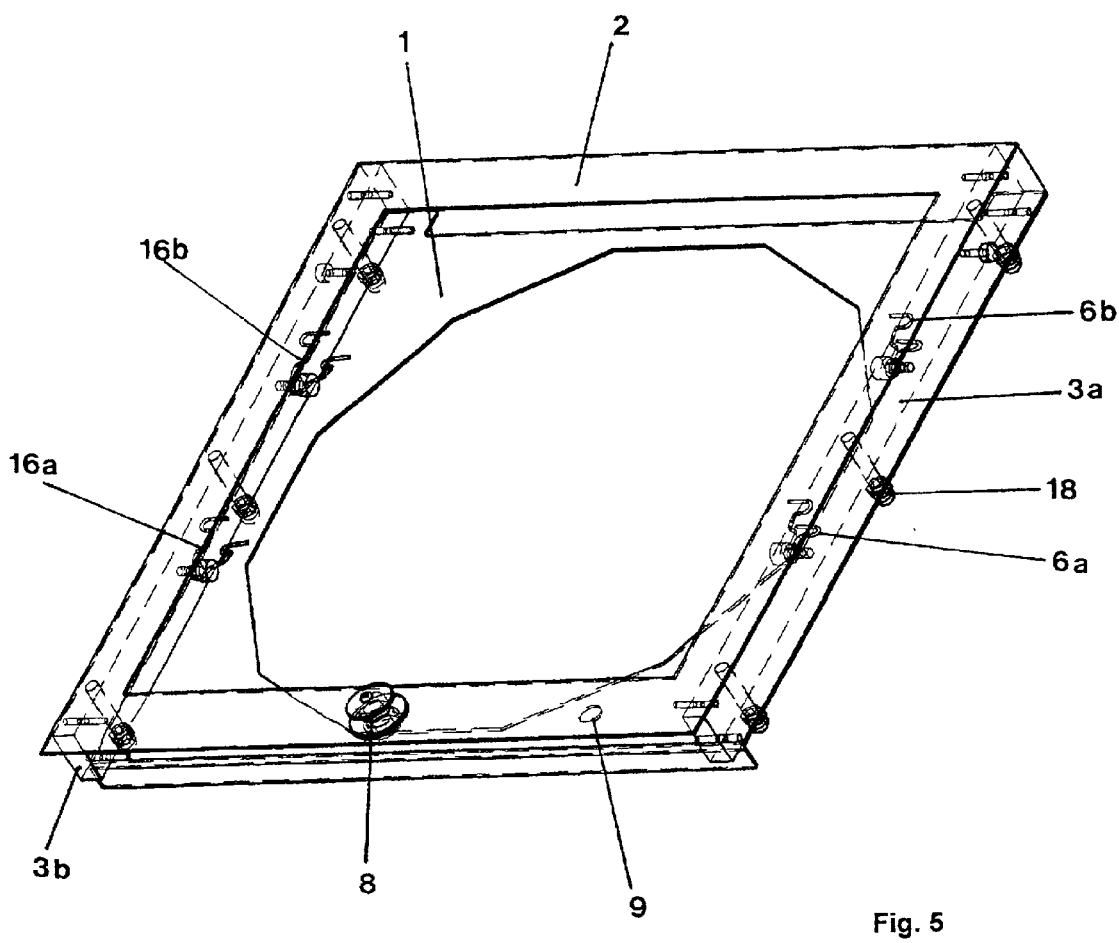
Figure 6:
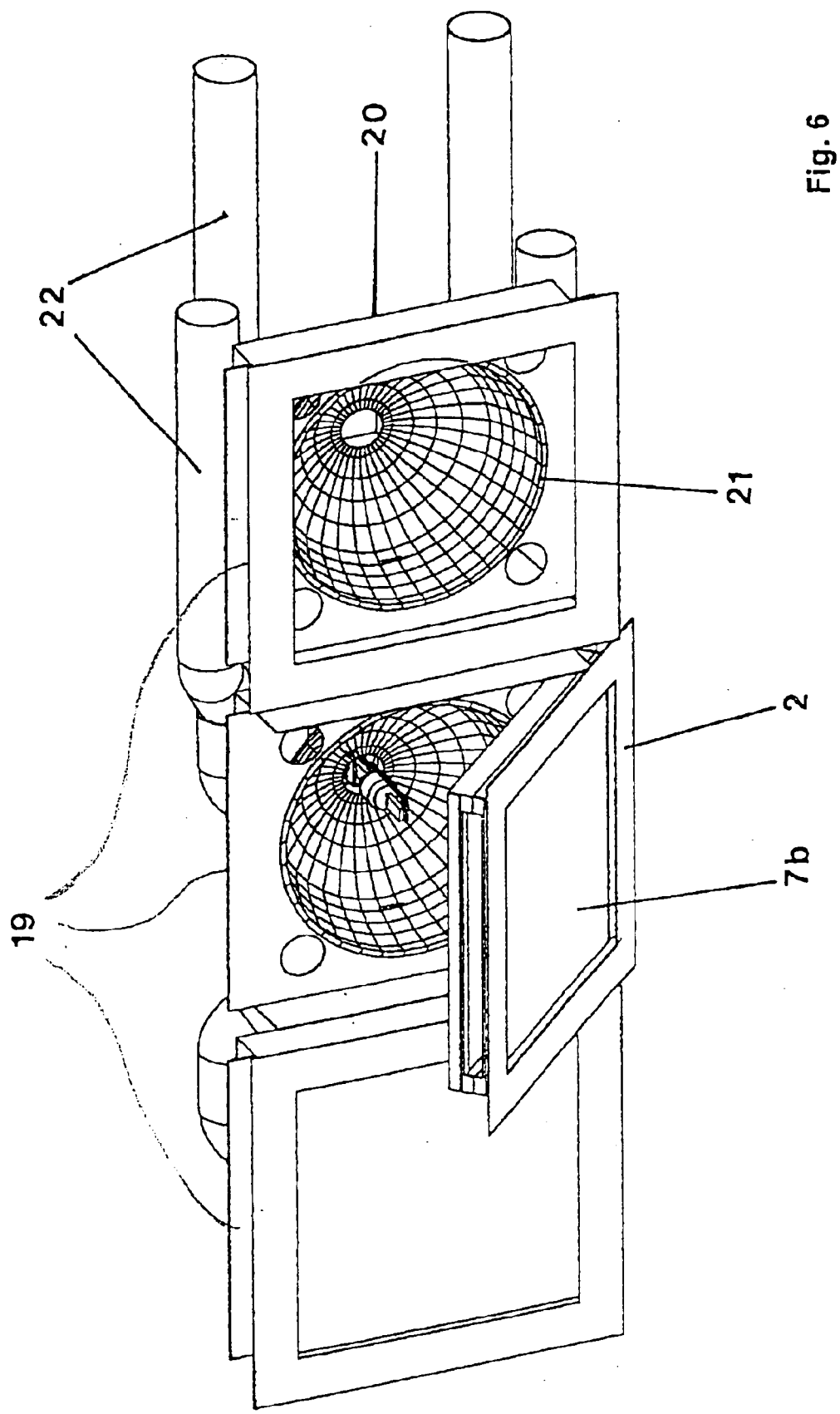
Figure 7:
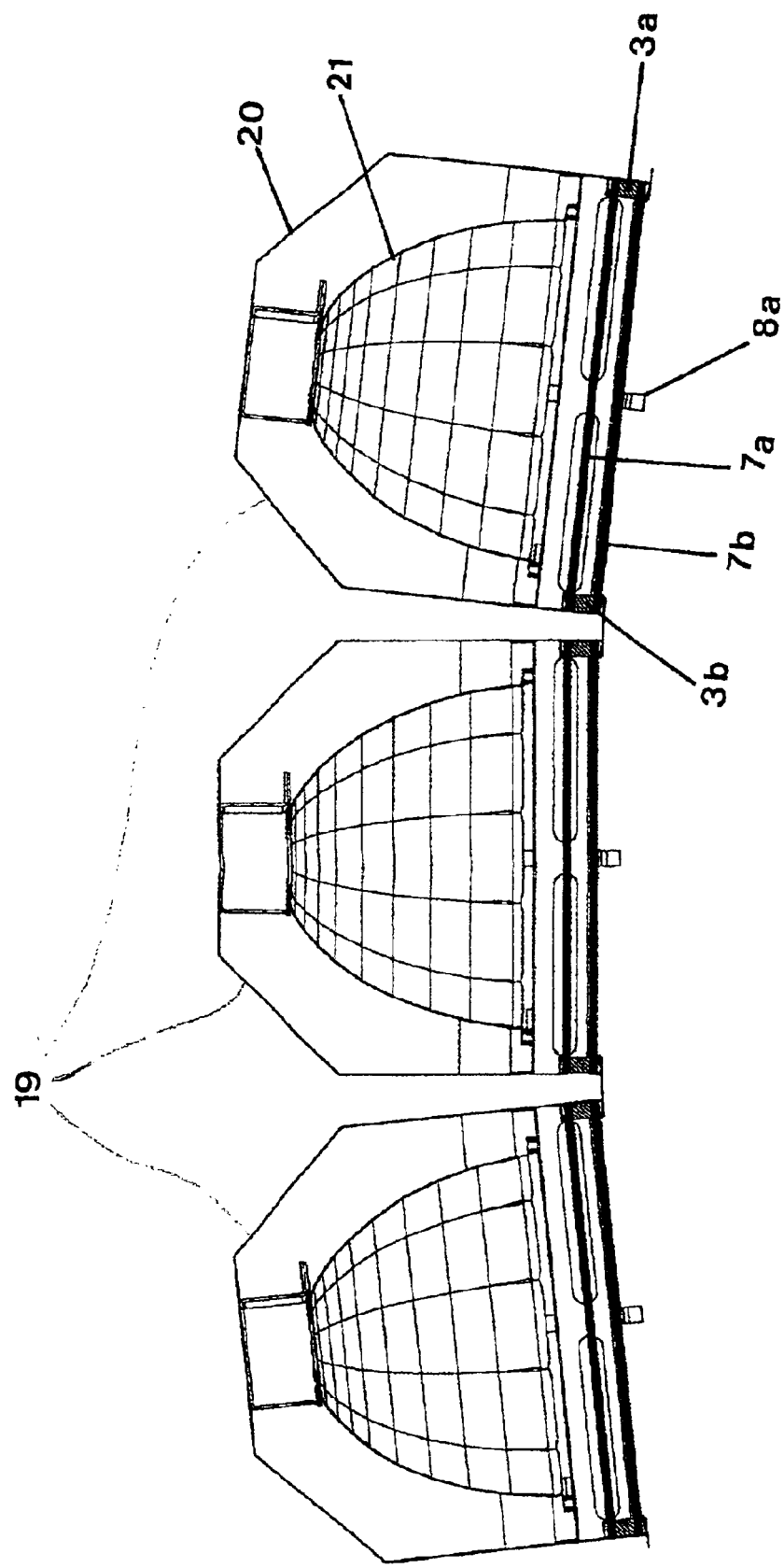
Figure 8:
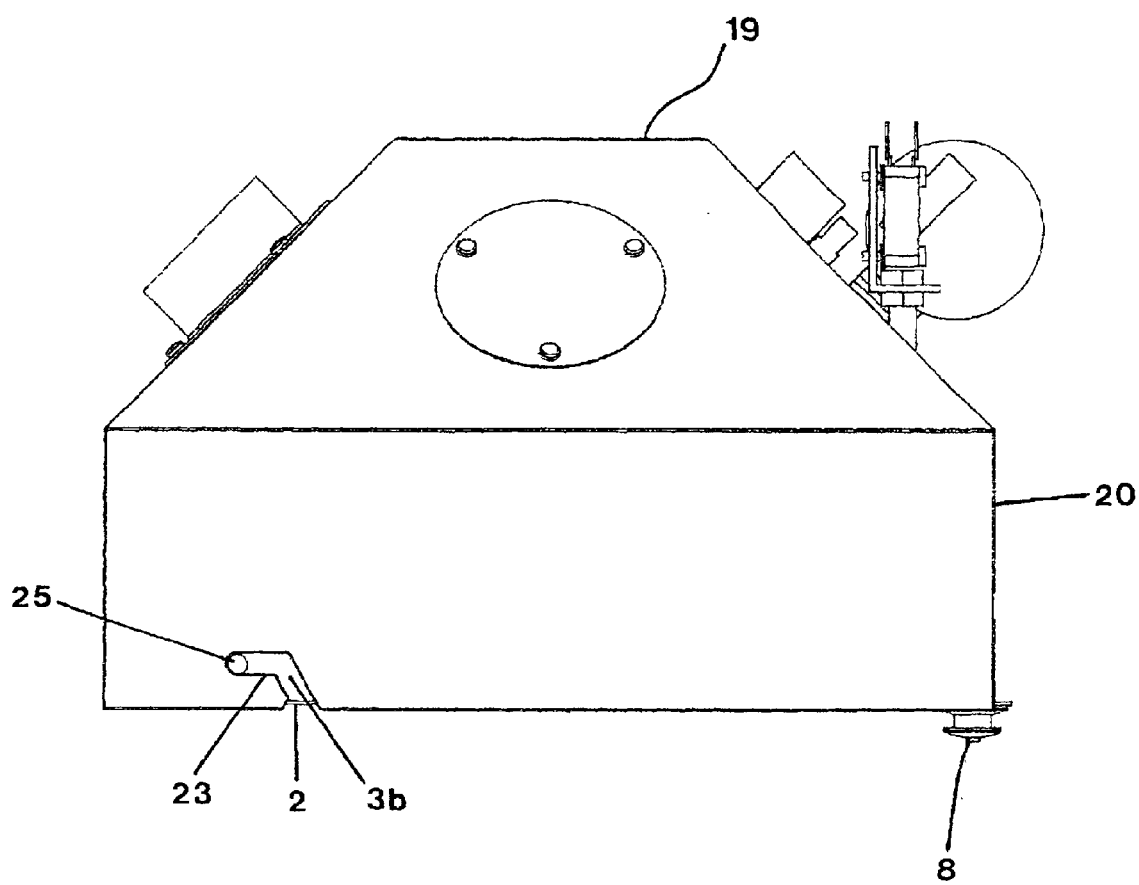

FIG. 4 shows a rectangular frame system with double spring clips according to FIG. 3, FIG. 4a shows the rectangular frame system of FIG. 4 in section, FIG. 5 shows the rectangular frame system of FIG. 4 in a tridimensional view, FIG. 6 shows a tridimensional view of several tanning modules, FIG. 7 shows three tanning modules, arranged as in FIG. 3, in section, FIG. 8 shows a tanning module with an opening for hooking the frame system into it.

Figure 1:
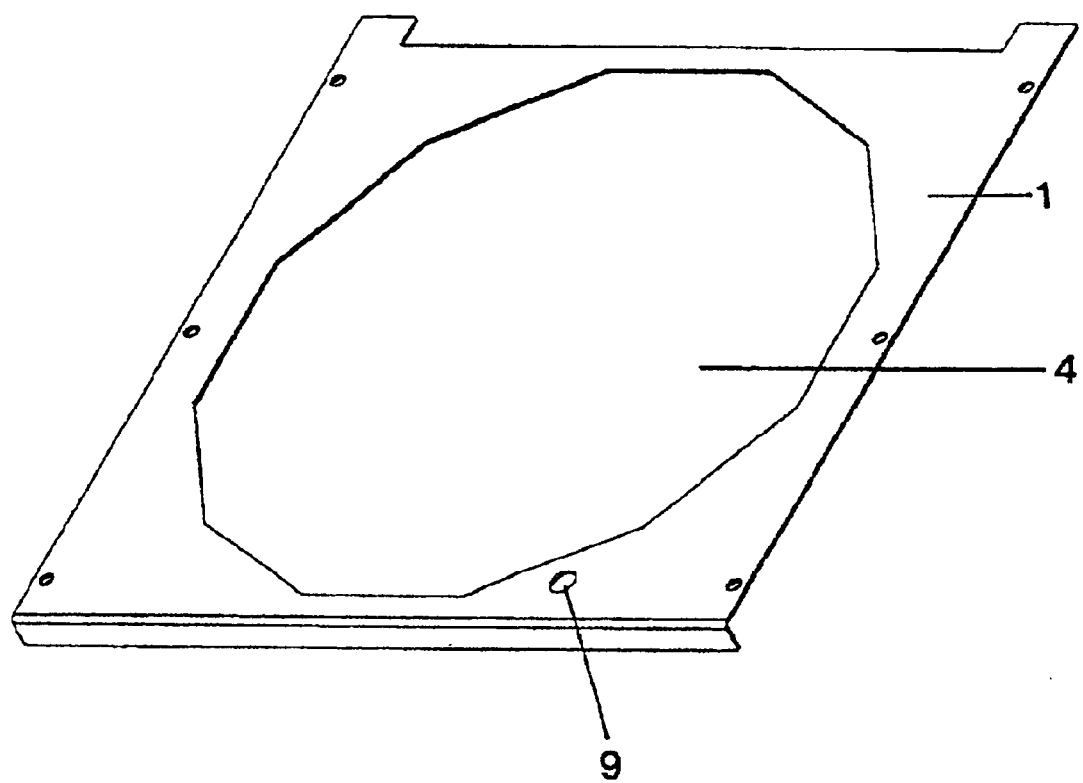
FIG. 1 shows a tridimensional view of the upper plate of the frame system.

FIG. 1 shows the upper plate 1 of the frame system in a tridimensional view, wherein the upper plate 1 has a first opening 4 for radiation emission. Moreover a bore 9 is present which permits the placement of a touch contact to protect the radiation filter against breakage.

Figure 2:
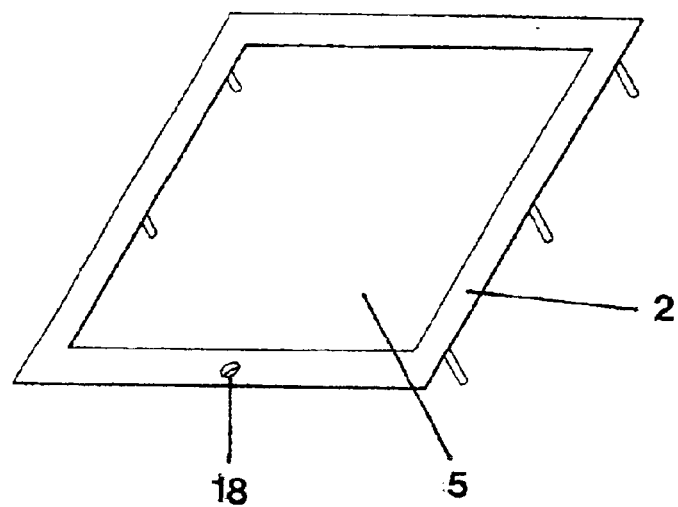
FIG. 2 shows a tridimensional view of the lower plate of the frame system.
Figure 2:
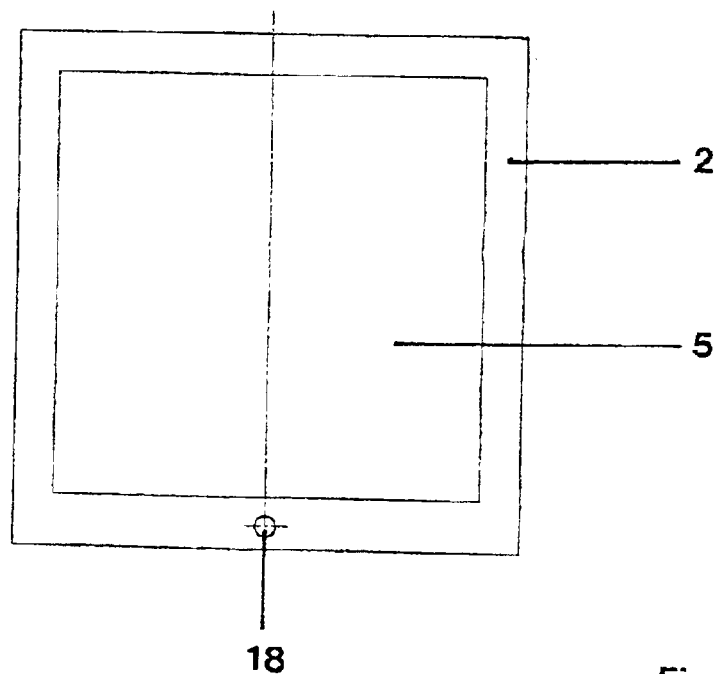

FIG. 2 shows the lower plate 2 of the frame system in a tridimensional view, wherein a second opening 5 is present. A threaded opening 18 is provided for attaching a snap fastener.

FIG. 2a shows the lower plate 2 from FIG. 2 in a plan view.

FIG. 3 shows a suitable double spring clip 6 which is bent from a metal wire.

FIG. 3a shows the double spring clip from FIG. 3 in a tridimensional view wherein the double spring clip 6 is to be fastened by its annular loop to a marginal member on the frame system.

FIG. 4 shows a rectangular frame system with double spring clips 6a, 6b, 16a, 16b as in FIG. 3, with the upper plate 1, the lower plate 2 and the snap fastener 8 in the form of a pushbutton.

FIG. 4a shows the rectangular frame system from FIG. 4 in section, the arrangement of a first radiation filter 7b and a second radiation filter 7a being shown. The upper plate 1 and the lower plate 2 are joined at the marginal member 3a by screws 18a.

FIG. 5 shows the rectangular frame system from FIG. 4 in a tridimensional view wherein an additional marginal member 3b can be seen.

FIG. 6 shows a tridimensional view of a plurality of tanning modules 19 with a housing 20 and the frame system of the invention. On the far left is shown a tanning module 19 with the frame system closed. In the center is a tanning module 19 with the frame system open including the tanning radiator, wherein the reflector 21, the lower plate 2 and the first radiation filter 7b can be seen. At the right end is shown a tanning module 19 without a radiation filter in the frame system and without a tanning radiator. All three tanning modules 19 are provided with air exhaust hoses 22.

FIG. 7 shows in section three tanning modules 19 which are arranged as in FIG. 6. A first radiation filter 7b and a second radiation filter 7a are present.

FIG. 8 shows a tanning module 19 with an opening 23 in the housing 20 for hooking on the frame system. The lower plate 2 and the marginal member 3b can be seen in the opening 23. The frame system is hooked in the opening 23 by a pin 25.

It is claimed:

1. A rectangular frame system with one to two discoid radiation filters for filtering the spectrum of a tanning radiator, with an upper plate, a lower plate and two to three marginal members wherein two marginal members lie opposite one another and the join the upper plate to the lower plate the upper plate having a first opening whose perimeter describes a circle, an ellipse, a rectangle or a polygon, and the lower plate has a rectangular second opening, the second opening having a greater area than the first opening, and on the two oppositely lying marginal members, which border on the side of the frame system at which no marginal member is provided, at least two double spring clips are arranged such that between the lower plate and the double spring clips a first radiation filter is clamped.

2. A rectangular frame system according to claim 1, wherein the first radiation filter is an interference filter.

3. A rectangular frame system according to claim 1, wherein the first radiation filter is of rectangular shape.

4. A rectangular frame system according to claim 1, wherein the first radiation filter has a width and a length ranging from 215 mm to 240 mm.

5. A rectangular frame system according to claim 4, wherein the first radiation filter has a width of 225 mm and a length of 230 mm.

6. A rectangular frame system according to claim 1, wherein a second radiation filter is clamped between the upper plate and the double spring clips.

7. A rectangular frame system according to claim 6, wherein the second radiation filter is an ultraviolet filter or an infrared filter.

8. A rectangular frame system according to claim 7, wherein the second radiation filter is of rectangular shape.

9. A rectangular frame system according to claim 8, wherein the second radiation filter has a width and a length ranging from 215mm to 240 mm.

10. A rectangular frame system according to claim 9, wherein the second radiation filter has a width of 225 mm and a length of 230 mm.

11. A rectangular frame system according to claim 6, wherein the double spring clips are configured such that the second radiation filter can be inserted from the side of the frame at which no marginal member is present, between the upper plate and the double spring clips.

12. A rectangular frame system according to claim 6, wherein the first radiation filter has on its side facing away from the second radiation filter an imprint or an adhesive label.

13. A rectangular frame system according to 12, wherein the imprint or label has an opaque marginal area.

14. A rectangular frame system according to claim 1, wherein the double spring clips are arranged half-way between the upper plate and the lower plate.

15. A rectangular frame system according to claim 1, wherein the double spring clip is formed from at least one bent metal wire.

16. A rectangular frame system according to claim 15, wherein the double spring clip is shaped according to FIG. 3a.

17. A rectangular frame system according to claim 15, wherein the double spring clip is shaped according to FIG. 3.

18. A rectangular frame system according to claim 1, wherein the double spring clip is formed from at least one flat spring plate.

19. A rectangular frame system according to claim 1, wherein the double spring clips are configured such that the first radiation filter can be inserted from the side of the frame system on which no marginal member is present, between the lower plate and the double spring clips.

20. A rectangular frame system according to claim 1, wherein on the side of the frame system at which no marginal member is present a device is provided to prevent the one to two radiation filters from slipping back.

21. A rectangular frame system according to claim 1, wherein on the side of the frame system that is opposite the side on which no marginal member is present, a device is provided and/or a third marginal member to prevent the dropping out of the one to two radiation filters.

22. A tanning module with a housing, a tridimensional reflector disposed on or in the housing, and with a rectangular frame system according to claim 1, on one side of the housing, wherein the first radiation filter covers the radiation emitting area of the reflector and the lower plate faces away from the reflector.

23. A tanning module according to claim 22, wherein the rectangular frame system can be released from the housing through a swivelling mechanism.

24. A tanning module according to claim 23, wherein the rectangular frame system is hooked into the housing.

25. A tanning module according to claim 24, wherein the rectangular frame system is hooked into an opening according to FIG. 8 in the housing.

26. A tanning module according to claim 23, wherein the rectangular frame system is fixed in position by means of a snap mechanism.

27. A tanning module according to claim 22, wherein a perimeter of the reflector parallel to the radiation emitting area describes a circle, an ellipse, a rectangle or a polygon.

28. A tanning module according to claim 27, wherein the reflector is formed of facets and the perimeter of the reflector parallel to the radiation emitting area describes a polygon with twelve corners.

29. A tanning module according to claim 28, wherein the reflector has a height of 90 mm to 95 mm, and the dodecagon has in the plane of the radiation emitting area a maximum diameter (corner to corner) ranging from 210 to 230 mm.

30. A tanning module according to claim 29, wherein the reflector has a height of 93.6 mm.

31. A tanning module according to claim 29, wherein the dodecagon has in the plane of the radiation emitting area a maximum diameter (corner to corner) of 210 mm.

32. A tanning module according to claim 28, wherein the reflector has a height ranging from 110 mm to 125 mm, and the dodecagon has in the plane of the radiation emitting area a maximum diameter (corner to corner) ranging from 170 mm to 200 mm.

33. A tanning module according to claim 32, wherein the reflector has a height of 118.7 mm.

34. A tanning module according to claim 32, wherein the dodecagon has in the plane of the radiation emitting area a maximum diameter (corner to corner) of 184 mm.

35. A tanning module according to claim 28, wherein the reflector has a height ranging from 75 mm to 90 mm, and the dodecagon has in the plane of the radiation emitting area a maximum diameter (corner to corner) ranging from 205 mm to 235 mm.

36. A tanning module according to claim 35, wherein the reflector has a height of 83.3 mm.

37. A tanning module according to claim 35, wherein the dodecagon has in the plane of the radiation emitting area a maximum diameter (corner to corner) of 220.

* * * * *